United States Patent [19]
Bogdanski

[11] Patent Number: 5,879,751
[45] Date of Patent: Mar. 9, 1999

[54] METHOD AND APPARATUS FOR MAKING ABSORBENT STRUCTURES HAVING DIVIDED PARTICULATE ZONES

[75] Inventor: Michael Scott Bogdanski, Schmitten, Germany

[73] Assignee: The Procter & Gamble Company, Cincinnati, Ohio

[21] Appl. No.: 574,168

[22] Filed: Dec. 18, 1995

[51] Int. Cl.⁶ .................................................. B05D 1/34
[52] U.S. Cl. ........................... 427/426; 427/189; 427/196
[58] Field of Search ................................ 427/426, 189, 427/196

[56] References Cited

U.S. PATENT DOCUMENTS

| | | | |
|---|---|---|---|
| 3,959,569 | 5/1976 | Burkholder, Jr. | 427/377 |
| 4,128,692 | 12/1978 | Reid | 427/212 |
| 4,377,230 | 3/1983 | Burkner . | |
| 4,467,012 | 8/1984 | Pedersen et al. | 427/392 |
| 4,551,191 | 11/1985 | Kock et al. . | |
| 4,578,068 | 3/1986 | Kramer et al. . | |
| 4,610,678 | 9/1986 | Weisman et al. . | |
| 4,715,918 | 12/1987 | Lang . | |
| 4,721,647 | 1/1988 | Nakanishi et al. | 427/385.5 |
| 4,748,076 | 5/1988 | Saotome | 427/389.9 |
| 4,767,586 | 8/1988 | Radwanski et al. . | |
| 4,770,344 | 9/1988 | Kaiser . | |
| 4,781,711 | 11/1988 | Houghton et al. . | |
| 4,834,735 | 5/1989 | Alemany et al. . | |
| 4,849,049 | 7/1989 | Colton . | |
| 4,891,249 | 1/1990 | McIntyre . | |
| 4,957,783 | 9/1990 | Gabryszewski . | |
| 4,988,344 | 1/1991 | Reising et al. . | |

(List continued on next page.)

FOREIGN PATENT DOCUMENTS

| | | |
|---|---|---|
| 0 198 683 | 10/1986 | European Pat. Off. . |
| 0 439 012 B1 | 7/1991 | European Pat. Off. . |
| 0 695 541 A1 | 2/1996 | European Pat. Off. . |
| 2636899 | 3/1977 | Germany . |
| 06-073535 | 9/1994 | Japan . |
| 06-075450 | 10/1994 | Japan . |
| 91/18137 | 11/1991 | WIPO . |
| WO 92/11831 | 7/1992 | WIPO . |
| WO 94/02092 | 2/1994 | WIPO . |

*Primary Examiner*—Shrive Beck
*Assistant Examiner*—Bret Chen
*Attorney, Agent, or Firm*—W. Scott Andes; E. Kelly Linman; Carl J. Roof

[57] ABSTRACT

A method and apparatus is disclosed for making absorbent structures having a layer of discrete particulate absorbent material which is divided into two or more bands separated by a substantially particulate-free zone. The method of making such absorbent structures comprises the steps of first generating an initial particle suspension comprising a two-phase fluid of particles of absorbent gelling material suspended in a gas (such as air) flowing in an inlet duct. The initial particle suspension is then divided into multiple final particle suspensions in corresponding multiple branch ducts, each of the final particle suspensions having a given percentage of particles as a function of cross-sectional area of the inlet duct. The particles in the final particle suspensions are substantially uniformly distributed as a function of cross-sectional position in the branch ducts. Finally, the suspended particles are filtered from the final particle suspensions by capturing them on a substrate such as a layer of tissue. An apparatus in accordance with the present invention for practicing the above method comprises an inlet duct, a particle suspension generator in fluid communication with the inlet duct for generating the initial particle suspension, at least two branch ducts in fluid communication with the inlet duct, and a particle suspension divider disposed within the inlet duct for dividing the initial particle suspension into multiple final particle suspensions in the branch ducts. In a preferred embodiment, the apparatus further comprises an adhesive delivery device for adhesively coating the particles in the final particle suspensions to form adhesively coated particles.

10 Claims, 6 Drawing Sheets

U.S. PATENT DOCUMENTS

| | | |
|---|---|---|
| 4,988,345 | 1/1991 | Reising . |
| 5,047,023 | 9/1991 | Berg . |
| 5,102,597 | 4/1992 | Roe et al. . |
| 5,129,356 | 7/1992 | Bandy et al. . |
| 5,180,622 | 1/1993 | Berg et al. . |
| 5,248,524 | 9/1993 | Soderlund . |
| 5,252,340 | 10/1993 | Honeycutt ............................... 427/212 |
| 5,271,780 | 12/1993 | Baigas, Jr. . |
| 5,304,161 | 4/1994 | Noel et al. . |
| 5,324,561 | 6/1994 | Rezai et al. . |
| 5,342,647 | 8/1994 | Heindel et al. ......................... 427/280 |
| 5,436,066 | 7/1995 | Chen ....................................... 427/213 | ns
METHOD AND APPARATUS FOR MAKING ABSORBENT STRUCTURES HAVING DIVIDED PARTICULATE ZONES

FIELD OF THE INVENTION

The present invention relates to an absorbent structure comprising at least one layer of discrete particulate absorbent material. More particularly, the present invention relates to a method and apparatus for making absorbent structures having a layer of discrete particulate absorbent material which is divided into two or more bands separated by a substantially particulate-free zone.

BACKGROUND OF THE INVENTION

Absorbent articles such as disposable diapers, incontinence pads, and catamenial napkins generally include an absorbent core for receiving and holding body exudates. The absorbent core typically includes a fibrous web, which can be a nonwoven, airlaid web of natural or synthetic fibers, or combinations thereof. A class of particulate absorbent materials known as superabsorbent polymers or absorbent gelling materials can be incorporated into the fibrous web to improve the absorption and retention characteristics of the fibrous web.

Because absorbent gelling materials are generally significantly more expensive than readily available natural or synthetic fiber materials (e.g., cellulose fibers), it is advantageous to reduce the quantity of absorbent gelling material in the core. Rather than uniformly distributing such particles throughout the entire core, it is desirable to distribute the particles in the absorbent core in a predetermined manner such that the particles are located where they will be most effective in acquiring and retaining body exudates.

While various means of forming uniformly distributed particle streams and applying them to portions of the absorbent core (such as entraining individual particles in an air stream) have been developed, these methods typically either require multiple feed mechanisms or overapplication of particles to selectively-adhesive-coated zones of the core. The use of multiple feed mechanisms multiplies the capital cost required to produce such absorbent cores, while the overapplication of particles to selective adhesive zones increases material waste and accompanying material costs.

Accordingly, it would be desirable to provide an improved method and apparatus for making absorbent structures having discrete bands or regions of absorbent particulate gelling materials separated by substantially particle-free zones which minimizes the equipment required.

It would also be desirable to provide an improved method and apparatus for making absorbent structures having discrete bands or regions of absorbent particulate gelling materials which reduces the amount of loose absorbent gelling material particles generated by the manufacturing process and provides reduced material waste.

SUMMARY OF THE INVENTION

The present invention provides a method and apparatus for making absorbent structures having a layer of discrete particulate absorbent material which is divided into two or more bands separated by a substantially particulate-free zone.

The method of making such absorbent structures comprises the steps of first generating an initial particle suspension comprising a two-phase fluid of particles of absorbent gelling material suspended in a gas (such as air) flowing in an inlet duct. The particles are substantially uniformly distributed in the gas as a function of cross-sectional position in the inlet duct. The initial particle suspension is then divided into multiple final particle suspensions in corresponding multiple branch ducts, each of the final particle suspensions having a given percentage of particles as a function of cross-sectional area of the inlet duct. The particles in the final particle suspensions are substantially uniformly distributed as a function of cross-sectional position in the branch ducts. Finally, the suspended particles are filtered from the final particle suspensions by capturing them on a substrate such as a layer of tissue.

In a preferred embodiment of this method, the final particle suspensions are directed through a stream of adhesive to form adhesively coated particles prior to being filtered from the final particle suspensions, followed by depositing the adhesively coated particles onto the substrate.

The initial particle suspension may be divided into two, three, or more final particle suspensions, and may preferably have approximately equivalent percentages of particles therein as a function of the cross-sectional area of the inlet duct.

An apparatus in accordance with the present invention for practicing the above method comprises an inlet duct, a particle suspension generator in fluid communication with the inlet duct for generating the initial particle suspension, at least two branch ducts in fluid communication with the inlet duct, and a particle suspension divider disposed within the inlet duct for dividing the initial particle suspension into multiple final particle suspensions in the branch ducts.

In a preferred embodiment, the apparatus further comprises an adhesive delivery device for adhesively coating the particles in the final particle suspensions to form adhesively coated particles.

The particle suspension divider preferably comprises a splitter plate for dividing the initial particle suspension into two, three, or more final particle suspensions in the branch ducts.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

FIG. 1 shows a partially cut-away plan view of an absorbent article according to the present invention;

FIG. 2 shows a top view of an absorbent structure according to the present invention;

FIGS. 3 and 4 respectively show a transverse cross-sectional view and a longitudinal cross-sectional view of the absorbent structure of FIG. 2, wherein the laminate is positioned at the user-facing side of the absorbent structure;

FIGS. 5 and 6 respectively show a transverse cross-sectional view and a longitudinal cross-sectional view of the absorbent structure of FIG. 2, wherein the laminate is positioned at the backsheet-facing side of the absorbent structure;

FIG. 7 shows a schematic transverse cross-sectional view of an absorbent article comprising an absorbent structure according to the present invention which includes a dusting layer;

FIG. 8 schematically shows a production line for forming absorbent articles comprising an absorbent structure according to the present invention;

FIG. 9 is a plan view of a nozzle assembly according to the present invention;

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, training pants, pull-on diapers, feminine hygiene garments such as sanitary napkins, and the like.

The absorbent article

Figure 1:
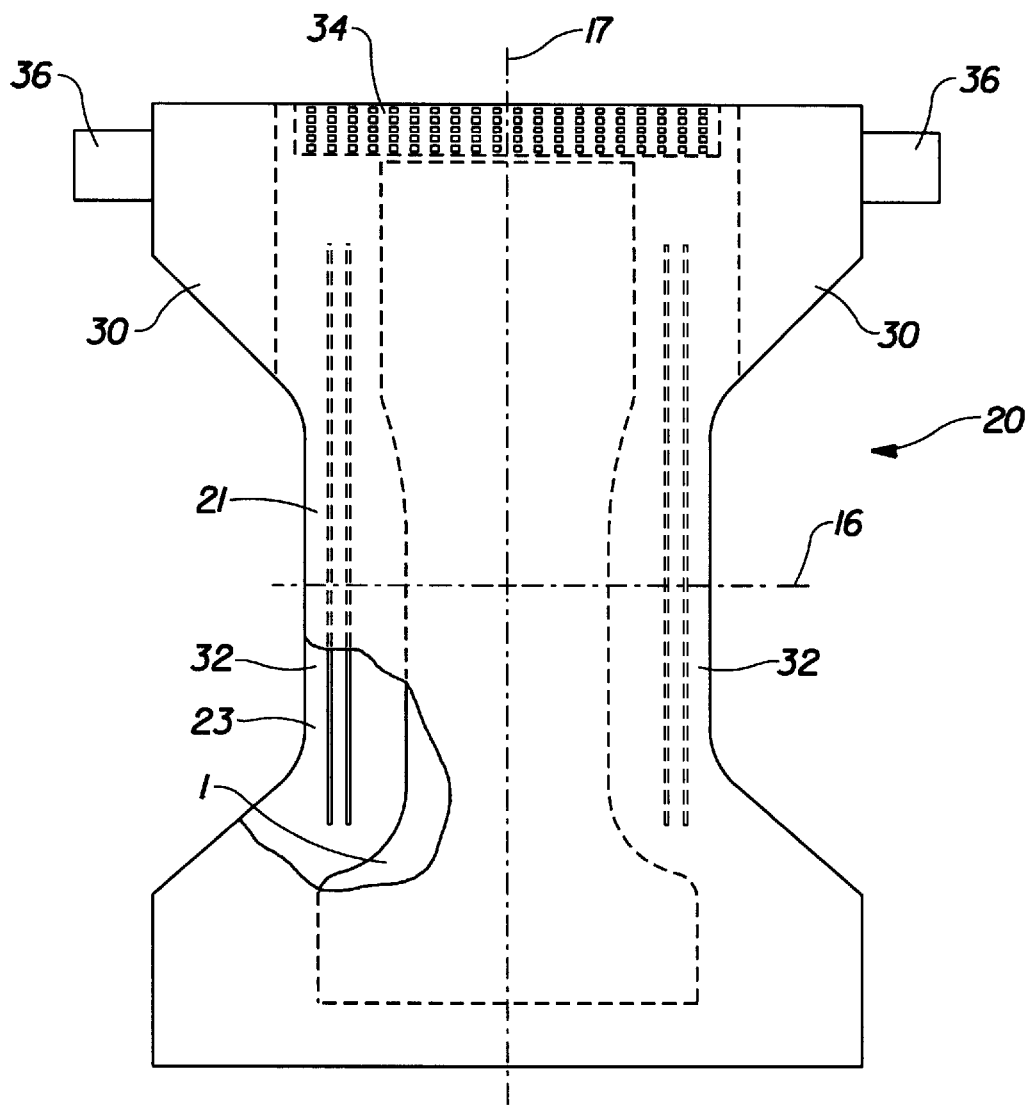

FIG. 1 is a plan view of the absorbent article 20, in particular a diaper, according to the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 comprises a liquid pervious topsheet 21 of which a part has been cut away to show the underlying structure. The core 1 is comprised between the topsheet 21 and backsheet 23. The diaper 20 further comprises elasticized side panels 30 which can elastically extend in the direction of the transverse center line 16, elasticized leg cuffs 32; an elastic waist feature 34; a fastening system generally multiply designated as 36.

FIG. 1 shows a preferred embodiment of the diaper 20 in which the topsheet 21 and the backsheet 23 have length and width dimensions generally larger than those of the absorbent structure 1. The topsheet 21 and the backsheet 23 extend beyond the edges of the absorbent structure 1 to thereby form the periphery of the diaper 20. While the topsheet 21, the backsheet 23, and the absorbent structure 1 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and commonly assigned U.S. patent application Ser. No. 07/715,152, "Absorbent Article With Dynamic Elastic Waist Feature Having A Predisposed Resilient Flexural Hinge", Kenneth B. Buell et al. filed Jun. 13, 1991; each of which is incorporated herein by reference.

Figure 2:
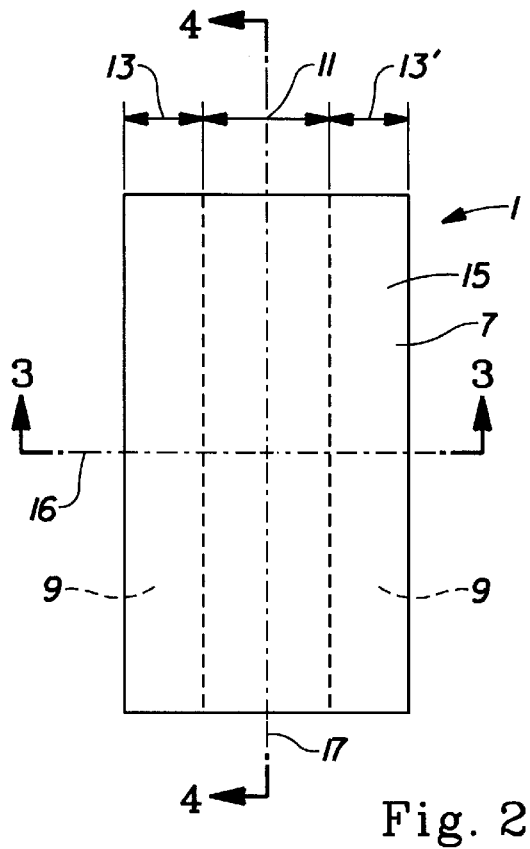
Figure 3:
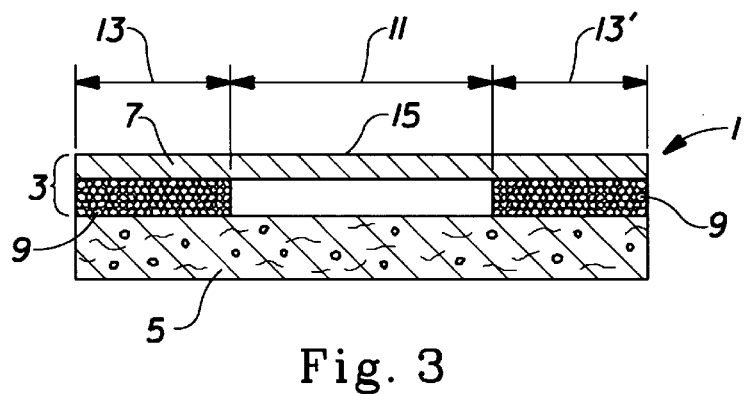
Figure 4:
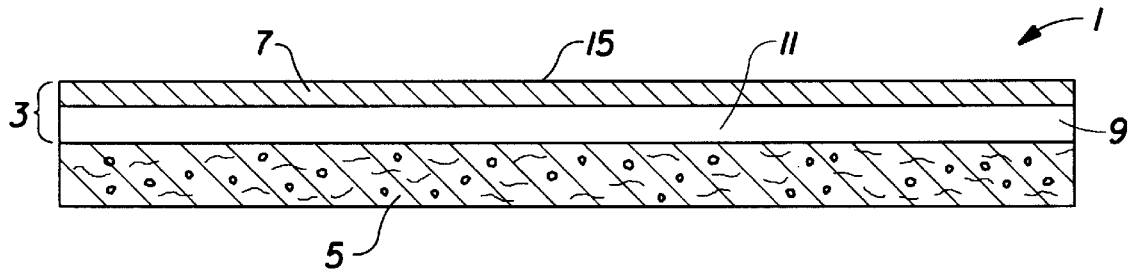

FIG. 2 shows a plan view of an absorbent structure 1, comprising storage zones 13,13' and central acquisition zone 11. FIGS. 3 and 4 show a cross-sectional view of the absorbent structure 1 along the transverse center line 16 and the longitudinal center line 17 respectively. The absorbent structure comprises an upper layer 3 and a lower layer 5. The upper layer 3 comprises a substrate 7 and a layer of absorbent gelling material particles 9 attached to the substrate 7. The combination of the substrate 7 and the absorbent gelling material particles attached thereto is also referred to as a "laminate". The upper layer 3 comprises a central acquisition zone 11 and a storage zone 13,13' bordering the acquisition zone 11 on either side. The average basis weight of the absorbent gelling material particles 7 in the acquisition zone is relatively low compared to the average basis weight of the absorbent gelling material particles in the storage zone 13,13'. Preferably no absorbent gelling material particles are present in the acquisition zone 11. The storage zone 13,13' can comprise an average basis weight of absorbent gelling material particles of more than 25 g/m2, preferably more than 40 g/m2, the average basis weight of the particles in the acquisition zone 11 being below 25 g/m2.

The lower layer 5 comprises a mixture of absorbent gelling material particles and fibers, which may be cellulose fluff pulp, synthetic fibers, or combinations thereof. The lower layer 5 is preferably formed by air laying. The upper layer 3 is preferably placed on top of the lower layer 5 in such a manner that the absorbent gelling material particles 9 are comprised between the substrate 7 and the lower layer 5. The substrate 7 prevents the absorbent gelling material particles, if they become detached from the substrate, to migrate to the user-facing side 15 of the structure 1 and prevents the particles from contacting the skin of the user.

Figure 5:
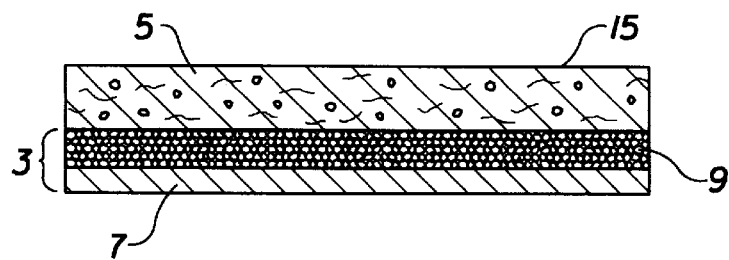
Figure 6:
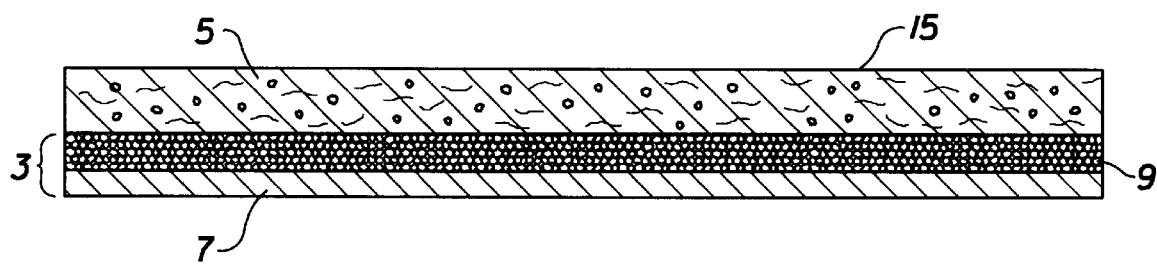

FIGS. 5 and 6 show cross-sectional views along the transverse centerline 16 and the longitudinal center line 17 of an embodiment of the absorbent structure wherein the laminate 3 is located below the mixed layer 5. The layer of absorbent gelling material particles 9 is uniformly distributed across the substrate 7. When desired, stripes, channels or other variations in the basis weight of the absorbent gelling material particles in the laminate 3 may be applied.

Figure 7:
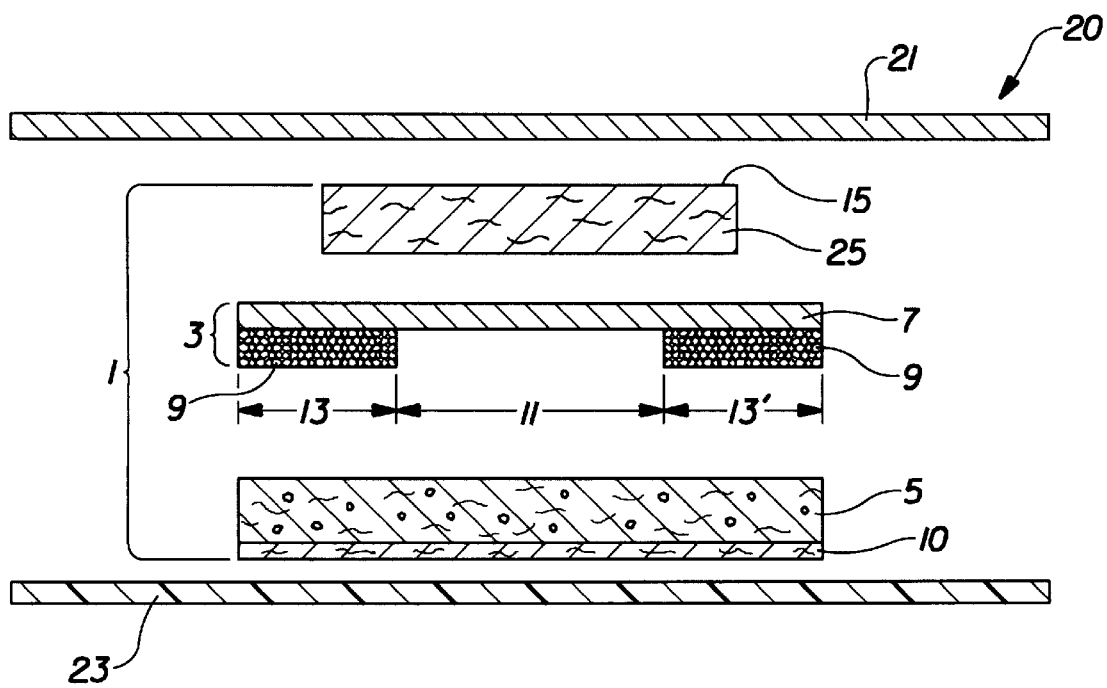

FIG. 7 shows a schematic cross-sectional view of a preferred embodiment of an absorbent article 20 comprising an absorbent structure 1 according to the present invention. The absorbent structure 1 is preferably encased between a liquid permeable topsheet 21 and a liquid-impermeable backsheet 23.

The topsheet

The topsheet 21 is positioned adjacent the body-facing surface 15 of the absorbent structure, or core, 1 and is preferably joined thereto and to the backsheet 23 by attachment means (not shown) such as those well known in the art. Suitable attachment means are described with respect to joining the backsheet 23 to the absorbent structure 1. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 21 and the backsheet 23 are joined directly to each other in the periphery of the absorbent article 20 and are indirectly joined together by directly joining them to the absorbent structure 1 by the attachment means (not shown).

The topsheet 21 is compliant, soft feeling, and non-irritating to the wearer's skin. Further, the topsheet 21 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 21 is made of a hydrophobic material to isolate the wearer's skin from liquids contained in the absorbent core 1. Preferably the topsheet is coated with a hydrophilic coating which is washed off the topsheet after being wetted. There are a number of manufacturing techniques which may be used to manufacture the topsheet 21. For example, the topsheet 21 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The backsheet

The backsheet 23 is positioned adjacent the garment surface of the absorbent structure 1 and is preferably joined thereto by attachment means (not shown) such as those well known in the art. For example, the backsheet 23 may be secured to the absorbent structure 1 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 23 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent structure 1 from wetting articles which contact the absorbent article 20 such as bedsheets and undergarments. The backsheet 23 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, Ind. The backsheet 23 is preferably embossed and/or matte finished to provide a more clothlike appearance. Further, the backsheet 23 may permit vapors to escape from the absorbent structure 1 (i.e., breathable) while still preventing exudates from passing through the backsheet 23.

The acquisition layer

In the embodiment of FIG. 7, the absorbent structure 1 comprises an upper acquisition layer 25. The acquisition layer 25 serves to quickly collect large gushes of liquids and to isolate these from the body of the wearer until these liquids have been absorbed in the underlying layers 5,7,9. The density of the acquisition layer 25 is preferably between 0.02 and 0.13 g/cm3, the basis weight being between 50 and 500 g/m2, depending on the volume of the gush that is to be taken up. A preferred material for the acquisition layer 25 is chemically stiffened cellulose material as described in EP-A-0 429 112 (Herron) U.S. Pat. No. 4,898,642 (Moore) and U.S. Pat. No. 4,889,597 (Bourbon). Further useful acquisition layers comprise open networks of thermally bonded air laid synthetic fibers, also referred to as "TBAL", as described in commonly assigned U.S. application Ser. No. 08/141,156 which was abandoned in favor of U.S. continuation application Ser. No. 08/479,096, issued Mar. 4, 1997 as U.S. Pat. No. 5,607,414. Other useful materials for use as an acquisition layer are described in PCT application no. PCT/EP94/01814, filed on Jun. 3, 1994. Further suitable materials for the acquisition layer are airfelt, mixtures of airfelt and synthetic fibers or for instance high loft nonwovens such as produced by Corovin GmbH, Postfach 1107, D-31201 Peine, Germany under the tradename COROLOFT.

An important property of the acquisition layer 25 is its ability to maintain a sufficient void volume for liquid uptake, even when wet. The fibers in the layer 25 should be sufficiently resilient to not collapse in their wet state upon compression.

The mixed layer

The mixed layer 5 may comprise any absorbent fibrous means which is generally compressible, conformable, non-irritating to the wearer's skin, and capable of absorbing and retaining liquids such as urine and other certain body exudates. The lower layer 5 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials which may be used in addition to the fibrous material included in the layer 5 are for instance creped cellulose wadding; meltblown polymers including coform; chemically stiffened, modified or cross-linked cellulosic fibers; tissue including tissue wraps and tissue laminates; absorbent foams; absorbent sponges, etc. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent structure 1 should, however, be compatible with the design loading and the intended use of the diaper 20. Further, the size and absorbent capacity of the absorbent structure 1 may be varied to accommodate wearers ranging from infants through adults. Exemplary mixed layers 5 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference.

In the embodiment as depicted in FIG. 7, a fibrous layer 10 that is substantially free of absorbent gelling material particles, also referred to as a "dusting layer", is located underneath the mixed layer 5. The dusting layer 10 and the fibrous matrix of the mixed layer 5 may be parts of a single homogeneous fibrous layer which has been formed by airlaying. However, for the purpose of the present invention, the dusting layer 10 is not considered as a part of the mixed layer 5. Forming an absorbent core comprising a mixed layer 5 and a dusting layer 10 has been described in U.S. Pat. No. 4,888,231 entitled "Absorbent Core Having A Dusting Layer" issued to Angstadt on Dec. 19, 1989.

The laminate

The substrate layer 7 of the laminate 3 can for example be formed by a nonwoven layer or by a tissue layer such as BOUNTY tissue as marketed by the Procter & Gamble Company, or such as a high wet-strength tissue of a basis weight of 22.5 g/m2 as produced by STREPP GmbH & Co, KG, D 5166 Kreuzau-Untermaubach, Germany, under the reference NCB. Alternatively, the substrate layer 7 is formed by a three-dimensional apertured thermoplastic film as described in EP-A-0 203 820 (Curro), EP-A-0 156 471 (Curro) and EP-A-0 141 654 (Koger II). Other suitable materials for forming the substrate layer 7 are high wet-strength nonwovens, such as polyolefin nonwovens.

The absorbent gelling material particles can be attached to the substrate by applying a layer of adhesive to the substrate 7, followed by deposition of the particles onto the layer of adhesive. The acquisition zone 11 is preferably substantially free of both adhesive and absorbent gelling material particles so that it maintains its ability to function in the acquisition role. In a presently preferred configuration, the basis weight of the particles 9 in the storage zone 13,13' is above 25 g/m2. In a preferred baby diaper 1, the laminate 3 of the absorbent structure comprises a total of between 1 and 4 grams of absorbent gelling material particles, such that the combined weight of the absorbent gelling material particles in the laminate 3 and in the mixed layer 5 forms at least 40% of the weight of the fibers in the mixed layer 5. The acquisition zone 11 may be formed by any pattern of open areas such as a number of channels or a number of circles, squares etc.

Method and apparatus for making an absorbent article

Figure 8:
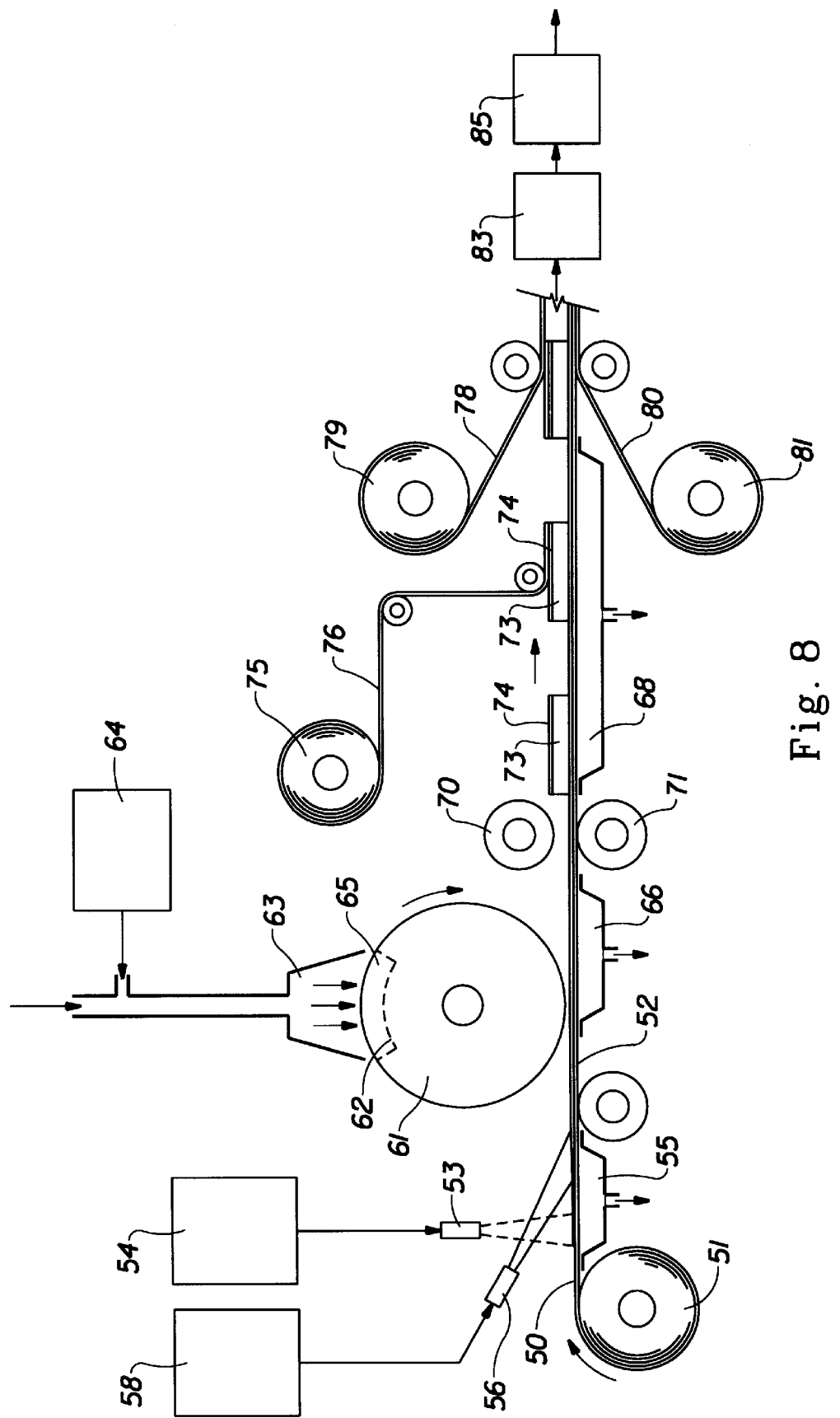

FIG. 8 schematically shows a process of making an absorbent article according to the present invention. A first tissue 50 is unwound from a supply roll 51. The tissue 50 forms the user-facing side 15 of the absorbent structure. Hot melt adhesive is supplied from a tank 54 to a nozzle 53 and is sprayed as meltblown fibers by the nozzle 53 in two longitudinal stripes parallel to the length direction of the tissue 50. Absorbent gelling material particles are supplied from a container 58, and are blown by an airgun 56 through the spray of adhesive exiting from the nozzle 53. The absorbent particles are directed by the airgun 56 in accordance with the present invention onto the same longitudinal parallel stripes of the tissue 50 as the adhesive. Suction device 55 aids in the laydown of the particulate material onto the tissue and also serves to collect stray particles. The adhesively coated absorbent gelling material particles are deposited in the storage zones of the substrate and form in combination with the tissue, the laminate 52. The functionality of airgun 56 according to the present invention is as described in the following section.

Cellulosic fibers are deposited via a chute 63 onto a laydown screen 62 of a rotating laydown drum 61. Absorbent gelling material particles are mixed into the airstream that carries the fibers from a storage container 64. On the laydown drum 61, the mixed layer 73, is formed. The absorbent gelling material particles from the container 64 are introduced in the fiber stream such that they are predominantly located on right-hand side of the chute 63. Hence the fibers that are first deposited onto the laydown screen 62 when the laydown cavity 64 is rotated underneath the chute, are not mixed with absorbent gelling material particles, and form the dusting layer 74. The absorbent element comprising the dusting layer 74 and the mixed layer 73, is placed onto the laminate 52. A suction device 66,68 draws the fibrous absorbent element 73 onto the laminate and maintains the absorbent elements in a defined position.

In a nip formed by a pair of calendar rolls 70 and 71, the absorbent elements 73 are compressed to the desired thickness and density. From a further supply roll 75, a pre-formed laminate 76 of any desired configuration is unwound and is placed on the backsheet-facing side of the absorbent element 73. The use of the pre-formed laminate 76 is optional and can be omitted when only a single laminate is desired at the user-facing side of the absorbent structure. Alternatively, the backsheet-facing laminate 76 can be made in an on-line manner similar to the way in which the laminate 52 is formed. Then the backsheet 78 and topsheet 80 are supplied from supply rolls 79 and 81 respectively, and are combined with the absorbent element 73 which now comprises the backsheet-facing laminate 76, the dusting layer 74, the mixed layer 73 and the topsheet-facing laminate 52. The continuous band of absorbent articles is then cut to form individual absorbent articles in a cutting unit which has not been depicted in this figure. The individual absorbent articles are folded in a folding unit 83 and are stacked, compressed and packed in a packing unit 85.

The process for forming the absorbent article according to the invention has only schematically been described. The process steps of attachment of elastic elements and provision of a tape fastening system have been omitted. A detailed description of a process for forming a mixed layer has been described in U.S. Pat. Nos. 4,765,780 and 4,764,325 (Angstadt).

Figure 9:
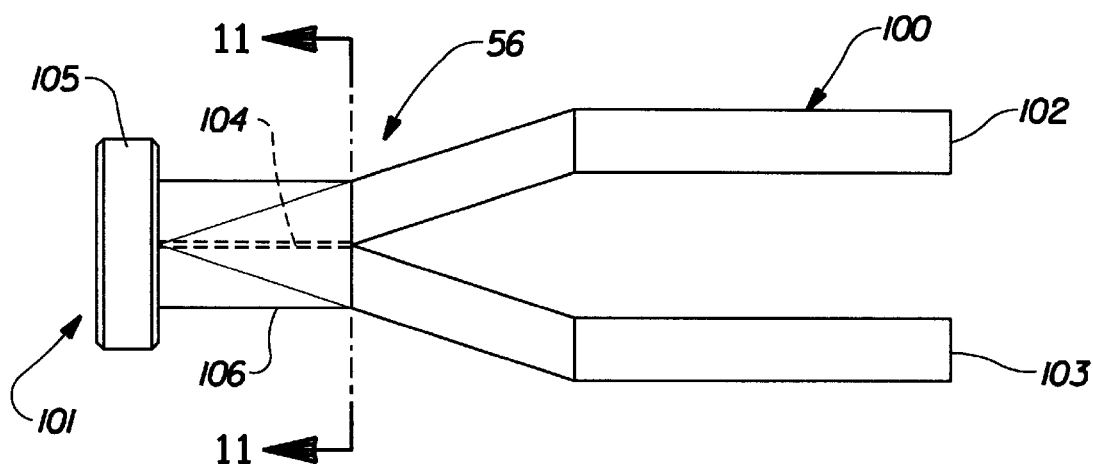
Figure 10:
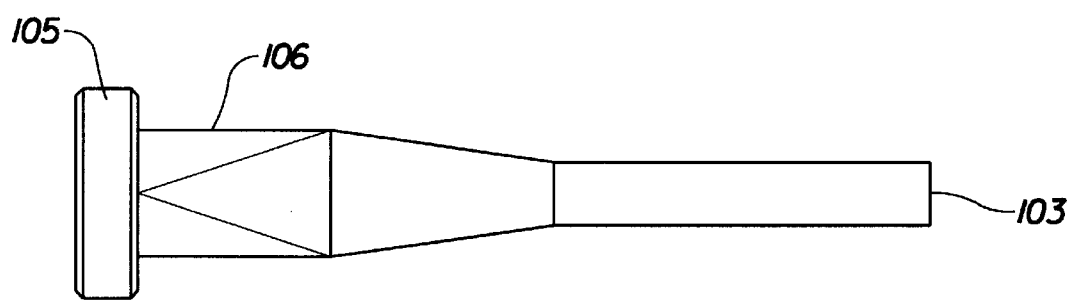
FIG. 10 is an elevational view of the nozzle assembly of FIG. 9.

Method and apparatus for making an absorbent structure (laminate) having divided particulate zones FIGS. 9 and 10 depict in greater detail the construction of an airgun 56 according to the present invention which is particularly useful in forming absorbent structures such as laminate 3.

As stated above, the laminate 3 preferably includes parallel stripes or bands 9 of absorbent gelling material particles adhered onto the substrate layer 7, separated by a substantially adhesive-free and particle-free acquisition zone 11. While it is preferred that acquisition zone 11 be substantially adhesive-free, a relatively small amount of adhesive may be applied to the acquisition zone to attach this zone to the underlying mixed layer for improvement of the integrity of the absorbent structure. A suitable adhesive is for instance hot melt adhesive as produced by Findley, Roosendaal, the Netherlands under the reference H 2127. The adhesive can be deposited via adhesive nozzle 53 as a melt-blown film which is blown at such high air speeds that the film breaks up into an open network of filaments as described in U.S. Pat. No. 4,573,986 (Minetola). Alternatively, a spiral pattern of adhesive may be deposited to obtain a liquid-permeable network of adhesive filaments as described in U.S. Pat. Nos. 3,911,173, 4,031,854, and 4,098,632 (all issued to Sprague).

In order to adhere the particles of absorbent gelling material particles to the substrate 7 according to the present invention, the particles are directed through a stream of adhesive prior to contacting the substrate to form adhesively coated particles. Subsequently, the adhesively coated particles are filtered out of the suspension by being captured or deposited onto the substrate. In this way good liquid permeability of the laminate is maintained, and very little blocking of liquid by the adhesive takes place.

The acquisition zone 11 can be maintained substantially free of adhesive by selective application of adhesive to the substrate for instance by application of two parallel stripes of adhesive covering the acquisition zones 13,13'. The adhesive can be applied by a single nozzle via a shielding element which blocks the part of the glue stream that is directed to the acquisition zone 11, or can be applied by two separate glue nozzles.

In the acquisition zone 11, preferably no absorbent gelling material particles are present. Accordingly, regardless of whether the acquisition zone 11 is entirely adhesive-free the airgun 56 according to the present invention provides multiple streams of absorbent gelling material particles in registry with the desired deposition regions 13, 13' of the laminate, and in registry with the adhesive pattern produced by the multiple glue nozzles or unblocked regions of the nozzle.

As more clearly depicted in FIG. 9, the airgun 56 preferably includes two elements: an eductor 101 and a splitter nozzle 100. Eductor 101 entrains individual particles of absorbent gelling material into an airstream to form or generate a substantially uniformly distributed suspension of particles. Eductors of this variety are commercially available under the trade designation Fox Venturi Eductor 1½" series, Model 300-SCE-55, Stainless Steel Version, manufactured by Fox Valve Development Corporation of Dover, N.J. Splitter nozzle 100 divides the substantially uniformly distributed suspension of particles into multiple substantially uniformly distributed suspensions of particles. As used herein, substantially uniformly distributed particle suspensions are those wherein the particles are substantially uniformly distributed as a function of cross-sectional position at any given cross-sectional location in a duct.

Figure 11:
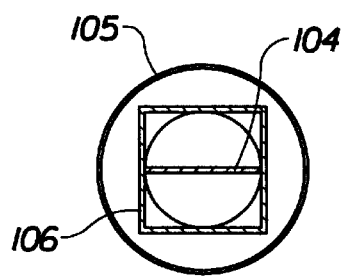
FIG. 11 is a cross-sectional view of the nozzle throat 106 of FIG. 9, illustrating the splitter plate 104.
Figure 12:
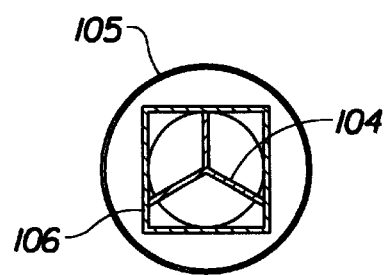
FIG. 12 is a cross-sectional view similar to FIG. 11 depicting an alternative splitter plate configuration.

In the configuration depicted in FIGS. 9 and 10, the splitter nozzle 100 includes two branch ducts 102 and 103 of approximately equal cross-sectional area. In the inlet duct (nozzle throat 106) a particle suspension divider (splitter plate 104) is positioned so as to divide the incoming substantially uniform particle suspension based upon cross sectional area into multiple particle suspensions, which then proceed through corresponding branch ducts. Nozzle throat 106 and splitter plate 104 may be sized and configured so as to produce multiple particle suspensions of equal, proportional, or diverse particle content and massflow. For example, in the configuration more clearly depicted in FIG. 11 (a cross section of nozzle throat 106) the splitter plate 104 is positioned in the nozzle throat 106 so as to divide the incoming cross-sectional area equally into two passages of equal cross sectional area (50% of the original cross-sectional area) which feed branch ducts 102 and 103. Accordingly, the particle suspension entering the splitter nozzle 100 from eductor 101 is equally divided into two particle suspensions for deposition onto the substrate 7.

Figure 13:
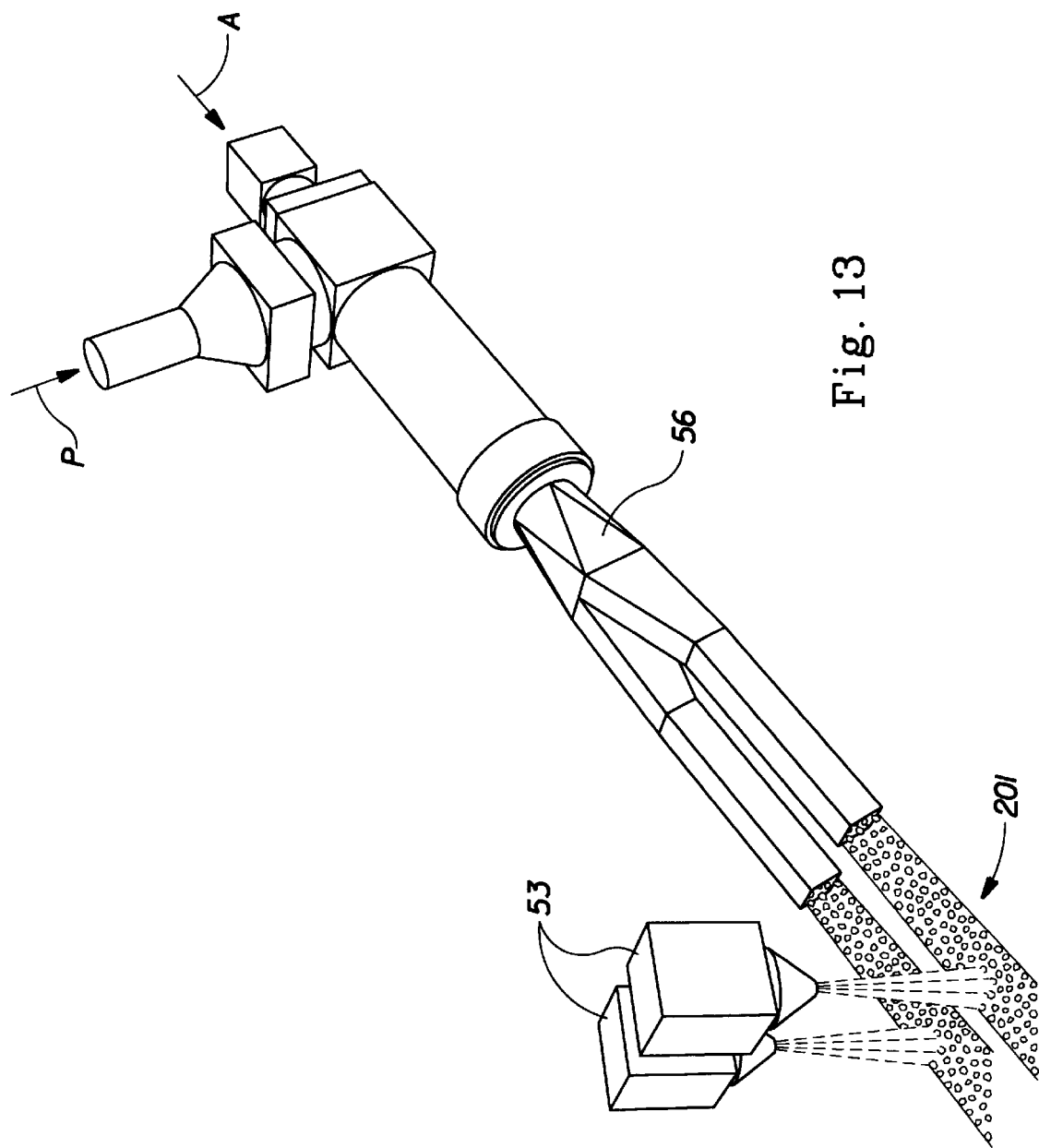
FIG. 13 is an enlarged perspective view depicting the relationship between the airgun 56 and the adhesive nozzle 53 depicted in FIG. 9 in operation.

Branch ducts 102 and 103 preferably have a length and geometry so as to equilibrate the particle distributions in the multiple flows after division in the event any non-uniformities are introduced into the flows, and are configured so as to discharge the particle suspensions in the desired orientation relative to one another and to the receiving surface. As depicted in FIG. 13, it is presently preferred that branch ducts direct the divided particle suspensions away from one another (being originally adjacent to one another in the same suspension) and then parallel to one another once again to form multiple parallel spaced particle suspensions. It is this spacing apart which provides the substantially particle free zone in the finished laminate corresponding to the acquisition zone 11.

FIG. 13 depicts the airgun 56 of FIG. 9 in operation when installed in a manufacturing setting such as depicted in FIG. 8. Note the relationship between the airgun 56 and the adhesive nozzle 53, and the divided particle streams 201 and 202.

In the event more than two outgoing particle streams are desired, splitter plate configurations may be developed so as to sectionally divide the incoming flow into 3 or more particle suspensions of the desired relative ratios and/or multiple splitter nozzles 100 could be utilized in sequence to subdivide already divided flows. One such splitter plate configuration for dividing an incoming flow into three flows is depicted in FIG. 12, wherein an incoming cross-sectional area is divided into three equal cross-sectional areas each 33% of the original cross-sectional area, each of which may feed a branch of the nozzle and thus generate three bands or strips of absorbent gelling material particles in a laminate.

Whether two, three, or more resulting flows are desired, it is presently preferred to accomplish the flow division via splitter plate orientations which are circumferentially symmetrically spaced. In the event that some non-uniformity of the incoming particle suspension occurs, such deviations in uniformity are frequently if not typically circumferentially symmetrical, i.e., a comparable distribution would be observed at various circumferential locations on a constant radius from the center of the incoming duct. Accordingly, by accomplishing flow division on a circumferentially symmetrical basis the likelihood of resulting variations in flow volume/density is reduced.

It is also possible to bond the absorbent gelling material particles without the use of an adhesive. The particles can be deposited onto a moist substrate 7 such that the particles absorb moisture on their surfaces and become tacky. Subsequent drying of the moist substrate 7 under application of pressure, results in attachment of the particles 9 to the substrate 7. In such a method of manufacture, the adhesive nozzle 53 would be omitted from the schematical illustration of FIG. 8, but the form and function of the airgun 56 would remain the same. In another alternative configuration wherein the particles are interconnected by application of an interparticle crosslink agent to form an interpartically crosslinked aggregate, the absorbent gelling material particles may be bonded to the substrate by the interparticle crosslink agent. This has been described in detail in commonly assigned U.S. application Ser. No. 08/142258 (Hseuh) issued Jul. 16, 1996 as U.S. Pat. No. 5,536,264.

A method of forming a multilayer laminate having a multiplicity of tissue layers and layers of absorbent gelling material particles encased between the tissue layers, is described in U.S. Pat. No. 4,578,068 (Kramer). In this structure, the absorbent gelling material particles are bonded to the tissue layers substantially entirely by fiber entrapment. A method for depositing absorbent gelling material particles onto a substrate has been described in U.S. Pat. No. 4,551,191 (Kock). Both of the aforementioned U.S. patents are hereby incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making an absorbent structure, said method comprising the steps of:

(a) generating an initial particle suspension comprising a two-phase fluid of particles suspended in a gas flowing in an inlet duct, said particles being substantially uniformly distributed in said gas as a function of cross-sectional position in said inlet duct;

(b) dividing said initial particle suspension into multiple final particle suspensions in corresponding multiple branch ducts, each of said final particle suspensions having a percentage of particles as a function of cross-sectional area of said inlet duct, said particles being substantially uniformly distributed in said gas as a function of cross-sectional position in said branch ducts; and (c) filtering said particles from said final particle suspensions by capturing said particles on a substrate.

2. The method according to claim 1, wherein said final particle suspensions are directed through a stream of adhesive to form adhesively coated particles prior to being filtered from said final particle suspensions, followed by depositing said adhesively coated particles onto said substrate.

3. The method according to claim 2, wherein said final particle suspensions are directed through corresponding multiple streams of adhesive.

4. The method according to claim 1, wherein said initial particle suspension is divided into two final particle suspensions.

5. A The method according to claim 1, wherein said initial particle suspension is divided into three final particle suspensions.

6. The method according to claim 1, wherein said final particle suspensions have approximately equivalent percentages of particles as a function of cross-sectional area of said inlet duct.

7. The method according to claim 1, wherein said initial particle suspension is circumferentially symmetrically divided into said final particle suspensions.

8. The method according to claim 1, wherein said final particle suspensions are directed away from one another and then directed parallel to one another to form parallel spaced particle suspensions prior to said capturing of said particles.

9. The method according to claim 1, wherein said gas comprises air and said particles comprise absorbent gelling material.

10. A method of making an absorbent structure, said method comprising the steps of:

(a) generating an initial particle suspension comprising a two-phase fluid of particles suspended in a gas flowing in an inlet duct, said particles being substantially uniformly distributed in said gas as a function of cross-sectional position in said inlet duct;

(b) dividing said initial particle suspension into two final particle suspensions in two corresponding branch ducts, each of said final particle suspensions having a percentage of particles as a function of cross-sectional area of said inlet duct, said particles being substantially uniformly distributed in said gas as a function of cross-sectional position in said branch ducts;

(c) directing said final particle suspensions through a stream of adhesive to form adhesively coated particles; and (d) filtering said adhesively coated particles from said final particle suspensions by depositing said adhesively coated particles on a substrate.

* * * * *